United States Patent
Dinkler et al.

(10) Patent No.: US 6,813,788 B2
(45) Date of Patent: Nov. 9, 2004

(54) VARIABLE LENGTH RADIOLUCENT SURGICAL TABLE EXTENSION

(75) Inventors: Charles E. Dinkler, Cincinnati, OH (US); Haring J. W. Nauta, Houston, TX (US)

(73) Assignees: Schaerer Mayfield USA, Inc., Cincinnati, OH (US); Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/610,310

(22) Filed: Jun. 30, 2003

(65) Prior Publication Data

US 2004/0055089 A1 Mar. 25, 2004

Related U.S. Application Data

(63) Continuation-in-part of application No. 09/543,878, filed on Apr. 6, 2000, now Pat. No. 6,584,630.

(51) Int. Cl.[7] .............................................. A61G 13/12
(52) U.S. Cl. .................................. 5/622; 5/601; 5/621
(58) Field of Search ................... 5/601, 632, 621–622, 5/638, 640; 108/69, 73, 152

(56) References Cited

U.S. PATENT DOCUMENTS

| | | |
|---|---|---|
| 1,171,713 A | 2/1916 | Gilkerson |
| 2,707,662 A | 5/1955 | Goldfield et al. |
| 2,753,233 A | 7/1956 | Rock |
| 2,840,429 A | 6/1958 | McDonald |
| 2,872,259 A | 2/1959 | Thorpe |
| 3,428,307 A | 2/1969 | Hunter et al. |
| 3,766,384 A | 10/1973 | Anderson |
| 4,076,230 A | 2/1978 | Pike |
| 4,333,638 A | 6/1982 | Gillotti |
| 4,484,571 A | 11/1984 | Velazquez |
| 4,500,146 A * | 2/1985 | Peterson ................... 312/257.1 |
| 4,506,872 A | 3/1985 | Westerberg et al. |
| 4,584,731 A | 4/1986 | Carter |
| 4,616,814 A | 10/1986 | Harwood-Nash et al. |
| 4,669,106 A | 5/1987 | Ammerman |
| 4,688,780 A | 8/1987 | Hanz |
| 4,727,328 A | 2/1988 | Carper et al. |
| 4,881,728 A | 11/1989 | Hunter |
| 4,910,819 A | 3/1990 | Brown |
| 4,914,682 A | 4/1990 | Blumenthal |
| 4,944,501 A | 7/1990 | Sireul et al. |
| 4,989,849 A | 2/1991 | Zupancic et al. |
| 5,088,706 A | 2/1992 | Jackson |
| 5,090,044 A | 2/1992 | Kobayashi |
| 5,155,758 A | 10/1992 | Vogl |
| 5,177,823 A | 1/1993 | Riach |
| 5,233,713 A | 8/1993 | Murphy et al. |
| 5,276,927 A | 1/1994 | Day |
| 5,335,384 A | 8/1994 | Foster et al. |
| 5,347,668 A | 9/1994 | Manning |
| 5,427,436 A | 6/1995 | Lloyd |
| 5,475,884 A | 12/1995 | Kirmse et al. |
| 5,499,415 A | 3/1996 | McKenna |
| 5,537,704 A | 7/1996 | Dinkler |

(List continued on next page.)

FOREIGN PATENT DOCUMENTS

| | | |
|---|---|---|
| EP | 0104591 A2 | 4/1984 |
| WO | WO9408704 | 4/1994 |
| WO | WO9911176 | 3/1999 |

*Primary Examiner*—Teri Pham Luu
*Assistant Examiner*—Fredrick Conley
(74) *Attorney, Agent, or Firm*—Wood, Herron & Evans, L.L.P.

(57) ABSTRACT

A surgical table extension has a radiolucent inner support member removably attachable to an end of a surgical table and extending outward therefrom in cantilever fashion. A radiolucent outer support member is mounted to the inner support member, and the outer support member is adjustable with respect to the inner support member to change the length of the table extension.

25 Claims, 4 Drawing Sheets

U.S. PATENT DOCUMENTS

| | | |
|---|---|---|
| 5,560,728 A | 10/1996 | McFadden |
| 5,655,238 A | 8/1997 | Stickley et al. |
| 5,661,859 A * | 9/1997 | Schaefer ........................ 5/621 |
| 5,675,851 A | 10/1997 | Feathers |
| 5,758,374 A | 6/1998 | Ronci |
| 5,774,916 A | 7/1998 | Kurhi |
| 6,003,174 A * | 12/1999 | Kantrowitz et al. ........... 5/601 |

* cited by examiner

VARIABLE LENGTH RADIOLUCENT SURGICAL TABLE EXTENSION

This application is a continuation-in-part of U.S. application Ser. No. 09/543,878, filed Apr. 6, 2000 now U.S. Pat. No. 6,584,630.

FIELD OF THE INVENTION

This invention relates to neurosurgical apparatus generally, and more particularly, to an improved apparatus for supporting an upper torso and head of a patient.

BACKGROUND OF THE INVENTION

With current medical practices, it is common for a patient to undergo a diagnostic scanning procedure, which is normally performed in a separate suite containing the scanning machine and dedicated to scanning procedures. The scanning machine may be a CT, MRI, or other scanning device. Thereafter, the scan data is utilized in a surgical planning process, which conventionally takes place at a location, for example, an office or an operating room. In some surgical procedures, the scanning data is utilized with a system for post processing the scan data acquired during imaging. Further, the imaging system may be located in a surgical suite, and the surgical planning performed before and during a surgical procedure utilizing the imaging system and scan data.

During the scanning procedure, the patient must maintain a perfectly still and motionless posture, and while most often, the patient simply lies on a scanning support table, in some situations, the patient may be supported in the desired scanning position with pads, straps or other supports. Further, the support on which the patient rests is normally radiolucent, that is, transparent to the scanning device, so that the support does not compromise the utility of the scanned image. Further, the patient support used for scanning normally translates with respect to the imaging device. Translation of the patient support permits the patient to be moved into the scanning field or zone of the scanning machine.

After the scanning process is completed, often the patient is then moved to an operating room which requires either that the patient walk, or be carried, for example, by transferring the patient from the scanning table to an operating table. Alternatively, as illustrated in U.S. Pat. No. 5,475,884, the patient may be supported on a portable support plate, which is easily moved between the scanning table and the operating table. The scan data is often used in a post processing imaging system for surgical planning purposes both prior to and during surgery. If during or after a surgical process, it is desired to scan a patient again, the patient must be moved from the operating room to the scanning suite, transferred to and from the operating table to the scanning table, and after scanning, transferred back to the operating table and returned to the operating room. The above process is cumbersome, time consuming and potentially risky for the patient.

Some newer scanning machines are substantially reduced in size. One such machine is shown in FIGS. 2 and 3 of U.S. Pat. No. 5,499,415, which show an annular-shaped scanner mounted on a wheel-supported frame, to enable the scanner to be used at multiple sites. Consequently, such scanning machines do not require their own suite or room, but instead, they may be used within the operating suite itself. Thus, in an operating room, the patient may be scanned; the surgical planning performed; an operative procedure executed; and the patient scanned again to determine the current status of the operative procedure. Based on the new scanned images obtained from the one or more "intraoperative" scans, the operative procedure can be continued and the above process repeated as necessary.

A limitation of the current state-of-the-art is that the posture of the patient during the scanning process is often different from the patient's posture during surgery. If a patient is positioned in one posture on a scanning table during the scanning process, and then is moved to an operating table, that motion of the patient may cause the position of the target to change with respect to the body surface. During surgery, this problem is compounded by tissue shifts attendant to the opening of body cavities, removal of body fluid or tissues and tissue retractions. Thus, while such motion may be small, any motion of the target will reduce or compromise the utility of the preoperative scan data.

The solution to these problems is to scan the patient in the operating room during surgery while the patient is maintained in the surgical posture, and further, to make successive intraoperative scans, as necessary, while still holding the patient in the same surgical posture.

While current scanning tables are radiolucent and provide a translation to move the patient into the scanning machine, such scanning tables do not have the accessories required to attach, support and stabilize surgical instrumentation and to properly support the patient's body in the desired surgical posture. Further, as presently known, scanning tables cannot be used as operating tables, and generally, operating tables are inappropriate for use as scanning tables.

Further, after a patient has been placed on an operating table, the patient's head is then mounted in a stabilization device, for example, a skull clamp. It is essential that the surgeon be able to position the patient very accurately. Minor changes in patient position have major consequences for optimal access and visualization during surgery. Different positions and orientations of the patient's head relative to the skull clamp often requires that patient's whole body be moved. Therefore, there is a need to be able to adjust the position and orientation of the patient's head with respect to the patient stabilization device without having to move the patient's body.

Consequently, there is a need to overcome the above-described problems and support a patient in a desired position in a manner which readily accommodates successive surgical and scanning procedures as well as intraoperative scans.

SUMMARY OF INVENTION

The present invention provides a variable length surgical table extension that is more flexible than known devices. The variable length surgical table extension of the present invention allows a patient stabilization device to be moved in many degrees of freedom including along a length of the table extension. Thus, a surgeon can easily and accurately position and orient a patient's head in the stabilization device independent of the patient's body position; and hence, minor adjustments of the patient's head with respect to the stabilization device can be made without having to move the patient's whole body. The variable length surgical table extension of the present invention is especially advantageous for use in neurosurgery and spinal surgery as well as intraoperative scanning procedures.

In accordance with the principles of the present invention and the described embodiments, a surgical table extension has a radiolucent inner support member removably attached to a longitudinal end of a surgical table and extending outward from the longitudinal end in cantilever fashion. A radiolucent outer support member is mounted to the inner support member, and the outer support member is adjustable with respect to the inner support member to change a length of the table extension. The surgical table and the table extension are movable relative to the scanning machine to locate the table extension within a scanning zone of a scanning machine.

In one aspect of the invention, a radiolucent patient stabilization device, such as a radiolucent skull clamp or a radiolucent horseshoe headrest, is supported by the outer support member.

Various additional advantages, objects and features of the invention will become more readily apparent to those of ordinary skill in the art upon consideration of the following detailed description of the presently described embodiments taken in conjunction with the accompanying drawings.

DETAILED DESCRIPTION OF THE INVENTION

Figure 1:
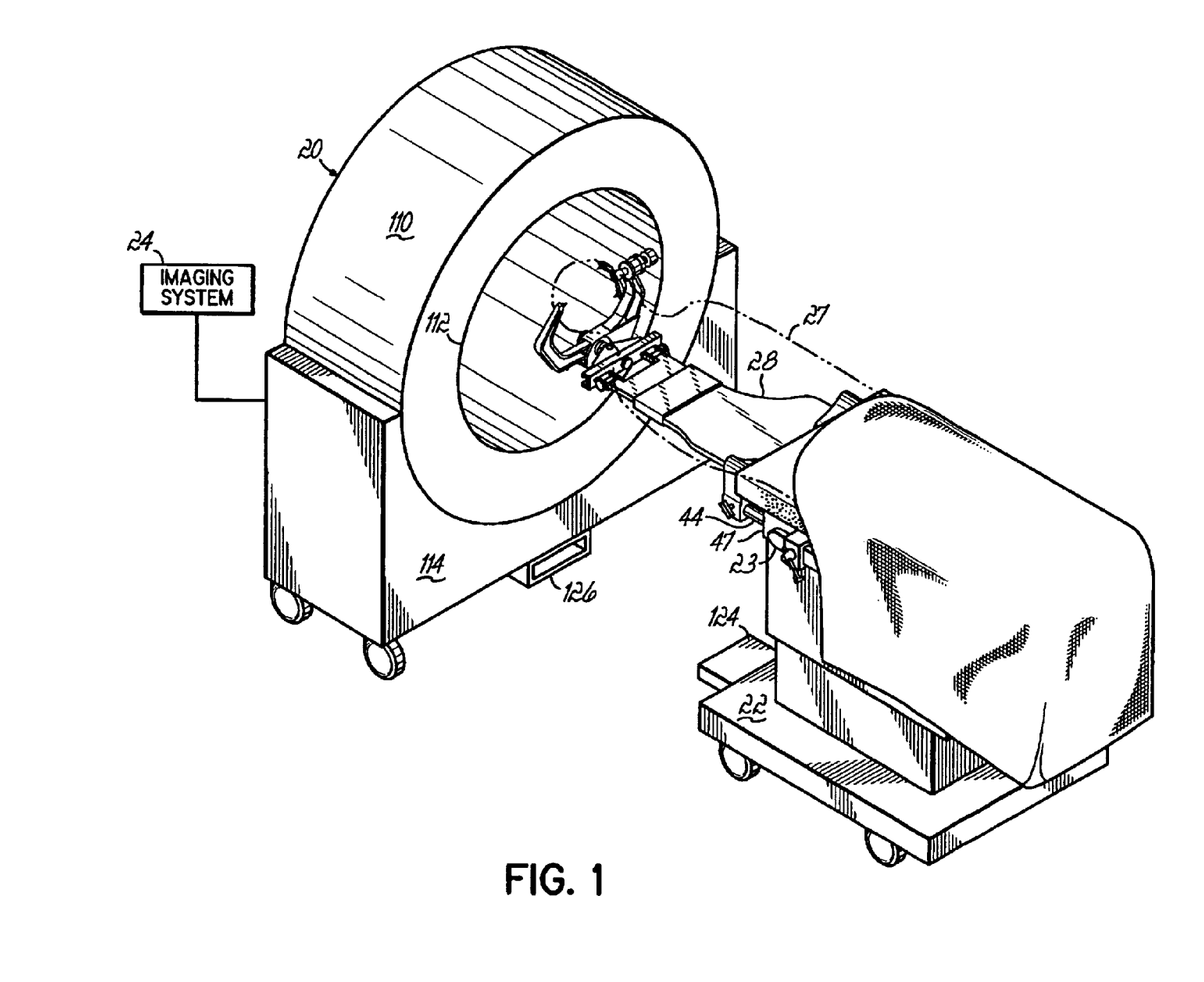
FIG. 1 is a perspective view of a known scanning system and surgical table including a variable length radiolucent table extension in accordance with the principles of the present invention.

Referring to FIG. 1, a portable CT scanning system 20 is located in an operating suite with an operating table 22. The CT scanning system may be either a mobile system such as that commercially available from Analogic of Peabody, Mass. or a stationary scanning system such as that commercially available from General Electric Medical Systems of Milwaukee, Wis. The operating table 22 may be one of many commercially available tables, for example, an operating table commercially available from Amsco of Erie, Pa., MDT Diagnostic Co. of N. Charleston, N.C., or other suppliers. The operating table has a lateral rail 23 extending along each side of the table to which retractors, clamps and other devices may be attached in a stable manner. A stereotactic image processing system 24, for example, the MAYFIELD-ACCISS image processing system, commercially available from Ohio Medical Instrument Company, Inc. of Cincinnati, Ohio is operatively connected to the scanner 20 and responsive to scan data provided by the CT system 20 to provide selected images on a display screen of the scan data along selected planes. Use of an imaging system 24 of this type is described in U.S. Pat. No. 5,695,501, which is expressly incorporated by reference herein, in its entirety. To facilitate the use of the operating table 22 with the CT system 20, one end of the operating table is used to support a radiolucent support member or table extension 28.

In use, referring to FIG. 1, the scanning system 20 and operating table 22 are brought into a surgical suite. The scanning system 20 has a toroid shape scanning element 110 with a central opening 112 defining an enclosed or encircled scanning zone with which the portion of the patient to be scanned is axially aligned. The scanning element 110 further has the capability of rotating or tilting within its base 114 with respect to a diametric horizontal axis. The distal end of the radiolucent table extension 28 is narrowed so that it can extend into the opening 112 without interference. If necessary, the head section (not shown) of the table 22 is removed therefrom, and the radiolucent table extension 28 is mounted to the table by inserting the support bars 44 into mating bores on the end surface 47 of the table 22. The patient 27 is then positioned on the table in a posture suitable for a surgical procedure. The radiolucent table extension 28 is adjustable such that the patient's upper torso and head are accessible for scanning and surgical procedures. The portion of the patient's anatomy on which the surgical procedure is to be performed may be stabilized by various clamps and restraining devices. Further, the radiolucent table extension 28 or the scanning element 110 may be tilted so that the desired posture and/or scanning plane is achieved.

When the desired surgical posture is achieved, often the patient will have already been scanned; and the surgical planning and procedure can be performed. Thereafter, a portion of the radiolucent table extension 28 is then moved into the opening 112, for a follow-up scan. The extent to which the table extension 28 is moved into the opening 112 depends on what portion of the head or upper torso is to be scanned. The initial alignment of the table extension 28 may be determined by visual inspection; and thereafter, a scan made to determine exactly whether, and to what extent, the table extension 28 may be out of alignment. Alternatively, the scanner may be equipped with LED's, or other sources of light, providing beams of light with which the table extension can be aligned. In another embodiment, the table 22 may have an alignment tab 124 which is moved into an alignment slot 124 on the scanner 110. When the tab 124 is properly seated in the slot 126, the table is properly aligned with the scanner 110. The scanning process is executed by the scanning machine moving the scanning element 110 incrementally in an axial direction and with each incremental displacement, a scan is taken. Thereafter, the radiolucent table extension 28 and the patient are removed from within the scanning element 110, either by moving the scanning machine 20 or the operating table 22. The scan data is then used in association with the imaging system 24 to plan the surgical procedure. The surgical procedure is then performed, and thereafter, the patient may be moved back into the scanning machine 20, and the scanning process repeated. The scanning and imaging system may be used to gauge the effectiveness of the surgical procedure; and if necessary, further procedures performed. The above process may be executed any number of times with the patient remaining in the desired position on the same patient support.

Thus, the above-described operating table and radiolucent table extension have a significant advantage of not only being able to support a patient during a scanning process, but also support the patient in the identical posture during a surgical procedure. The radiolucent table extension permits an operating table that is normally nonradiolucent and inappropriate for scanning purposes to be used with a scanning machine. Further, the table extension may be tilted to accommodate different desired surgical postures and is sized and shaped to readily fit within the opening of a scanning element, whether in a horizontal or tilted position. Further, not only does the table position permit successive scanning and operative procedures on the upper torso and head of a patient, but the radiolucent table extension 28 readily supports the patient in a prone or supine position. The above described system is illustrated in more detail in U.S. Pat. No. 6,003,174, is assigned to the assignee of the present invention and is hereby incorporated in its entirety by reference herein.

Figure 2:
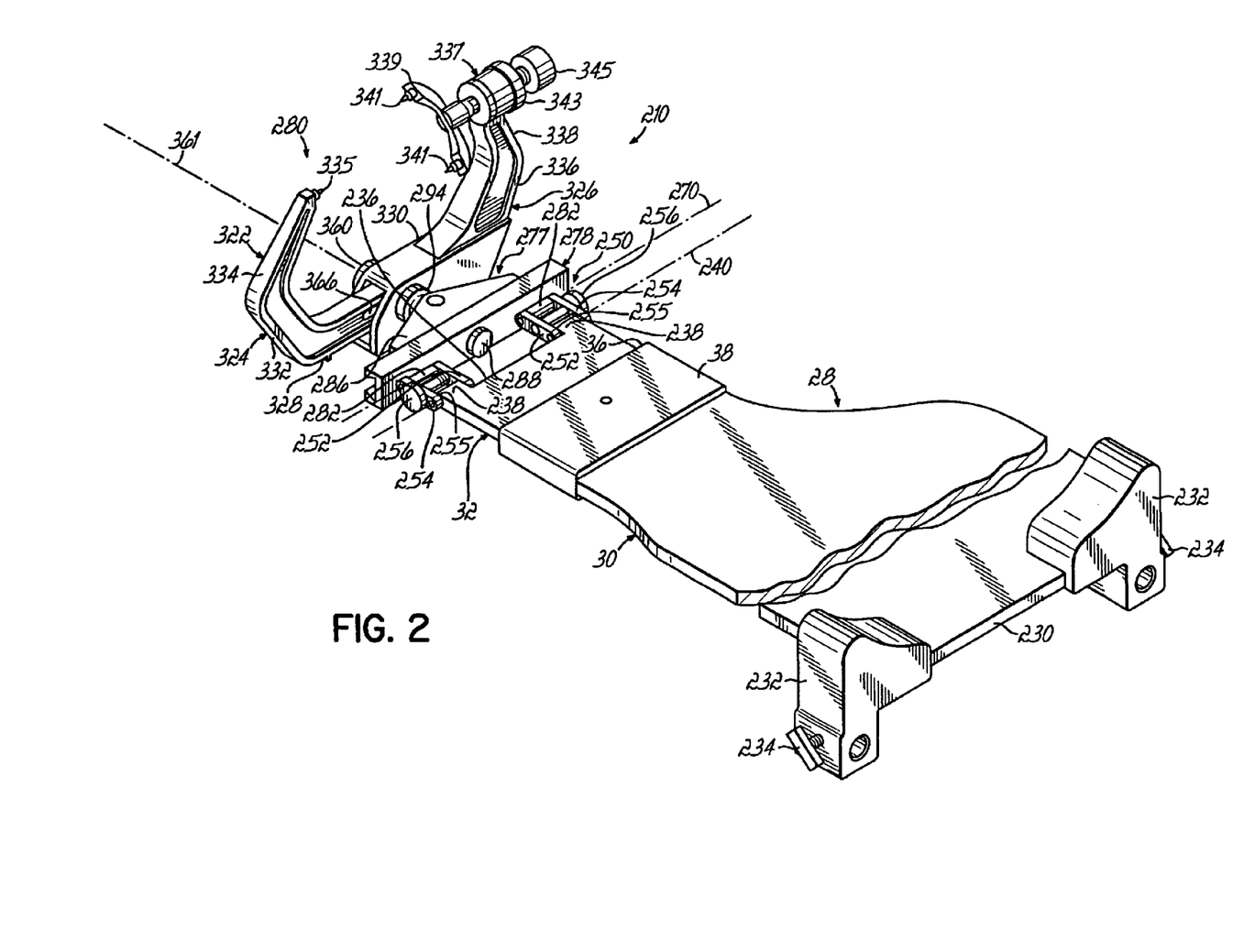
FIG. 2 is a perspective view of one embodiment having a radiolucent skull clamp mounted on the variable length radiolucent table extension of FIG. 1.

While the above described system has significant utility, there is a continuing effort to improve the flexibility and utility of the table extension 28. Referring to FIG. 2, the radiolucent table extension 28 is variable in length and has a radiolucent inner support member 30 connectable to the operating table 22 and a radiolucent outer support member 32. Attachable to an outboard or distal end 236 of the outer support member 32 is a radiolucent adaptor assembly 210 that supports a patient stabilization device 280, for example, a skull clamp. The inner support member 30 has an internal cavity or opening 34 on its outer end 36 that extends longitudinally inside the inner support member 30. The cavity 34 is located in a slightly enlarged portion 38 of the inner support member 30. The outer support member 32 has an inner end 40 that is sized and shaped to slide inside the opening 34. To facilitate movement of the outer support member inner end 40 in the cavity 34, the inside of the cavity 34 is lined with a low friction material, for example, a TEFLON material. Thus, by sliding the outer support member 32 with respect to the inner support member 30 in a direction parallel to a length or longitudinal axis 361 of the table extension 28, the length of the radiolucent table extension 28 can be easily changed.

Figure 3:
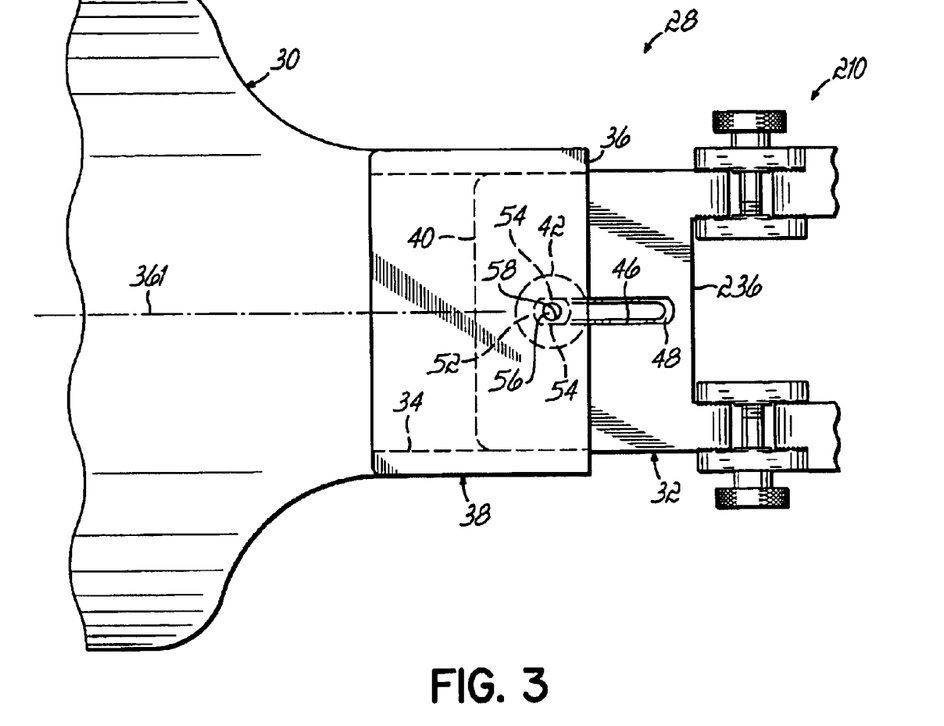
FIG. 3 is a top view of the variable length radiolucent table extension of FIG. 1.
Figure 4:
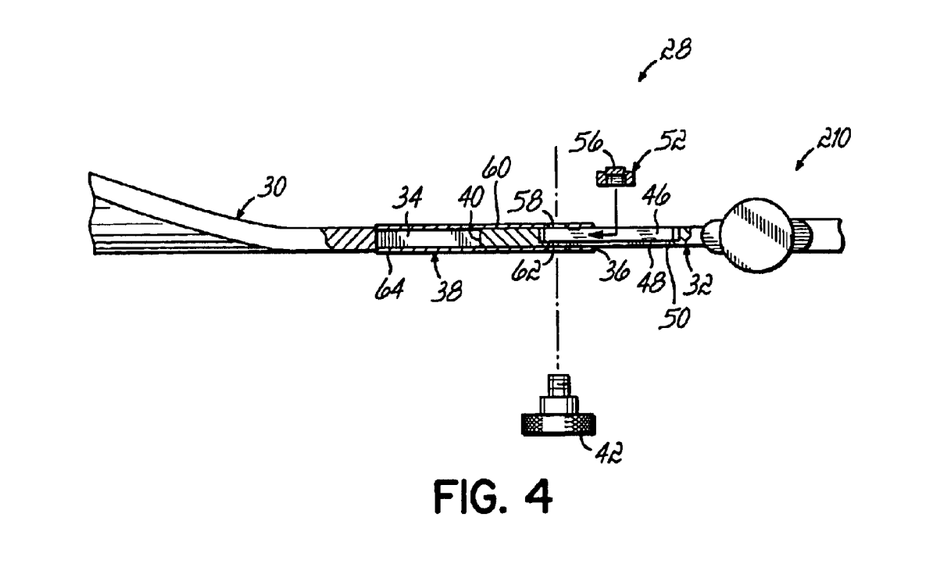
FIG. 4 is a side view of the variable length radiolucent table extension of FIG. 1 showing the locking apparatus disassembled.

After the table extension 28 is adjusted to a desired length, a locking screw 42 is tightened to secure the inner support member 30 with the outer support member 32. Referring to FIGS. 3 and 4, a slot 46 is disposed through the outer support member 32 such that a longitudinal centerline of the slot 46 is generally collinear with the longitudinal centerline 361. The slot 46 has an internal peripheral flange 48 that is contiguous with a lower side 50 of the outer support member 32. A threaded insert 52 is disposed in the slot 46 and rests on the peripheral flange 48. The insert 52 has opposed flat sides 54 that are adjacent sides of the slot 46 and prevent the threaded insert 52 from rotating. The threaded insert 52 further has an upward extending cylindrical stub 56 that is sized to fit in a hole 58 located in an upper wall 60 of the cavity 34. The locking screw 42 extends through a clearance hole 62 in a bottom wall 64 of the cavity 34 and is threaded into the threaded insert 52.

Thus, in adjusting the length of the table extension 28, the outer support member 32 and slot 46 are moved with respect to the stationary inner support section 30 and threaded insert 52. When the desired length is achieved, the locking screw 42 is tightened causing the threaded insert 52 in the inner support member 30 to clamp against the flange 48 on the outer support member 32, thereby locking the movable outer support member 32 with the fixed inner support member 30.

An improved system for mounting a radiolucent head clamp to the radiolucent table extension 28 is also illustrated in FIG. 2. A first, or inboard, end 230 of the inner support member 30 of the table extension 28 connects to the surgical table 22 (FIG. 1). This connection at the first end 230 occurs via a pair of spaced base mounts 232. Each of the base mounts 232 engages an inboard corner of the radiolucent table extension 28 and is shaped to receive an outwardly extending post or bar 44 (FIG. 1) extending from the surgical table 22. A threaded knob 234 tightens upon the inserted post on both sides of the surgical table 22 to securely mount the extension 28. Depending on the type of table 22, the manner of mounting the extension 28 may vary.

The second, or outboard, end 236 of the outer support member 32 of the radiolucent table extension 28 includes a pair of spaced radiolucent collars 238 aligned along a first connection axis 240. The first axis 240 is oriented horizontally and perpendicular to the longitudinal direction of the radiolucent table extension 28. The first connection axis 240 provides for hinged, or pivotal, movement of the radiolucent adaptor assembly 210, and everything else, including a skull clamp 280, connected thereto, relative to the radiolucent table extension 28.

To provide this hinged movement about the first connection axis 240, the radiolucent adaptor assembly 210 comprises a pair of spaced radiolucent adaptor subassemblies 250, each of the adaptor subassemblies 250 is associated with one of the spaced collars 238 of the table extension 28. Each subassembly 250 includes identically shaped, radiolucent interior and exterior pieces 252, 254, respectively, which are tightenable in a horizontal direction via a threaded knob 256. The knob 256 includes a threaded shaft (not shown) which extends through a central clearance bore (not shown) in the exterior piece 254 and engages a central threaded bore (not shown) in the interior piece 252. If desired, the arrangement of the respective interior and exterior pieces 252, 254 can be reversed, so long as the pieces 252, 254 are tightenable together upon the respective collars 238.

Along first axis 240, each of the interior and exterior pieces 252, 254, respectively, has a pair of parallel locator pins (not shown). The locator pins are sized to extend through clearance bores in the collars 238 along the connection axis 240, with a slip fit, so as to be rotatable relative to the collars 238. Together, the opposing locator pins of the respective interior and exterior pieces 252, 254 are held by the collars 238 along the first connection axis 240, so that upon tightening of each of the threaded knobs 256, the inwardly directed surfaces of the interior and exterior pieces 252, 254 engage the outwardly directed surfaces of the respective collars 238. Normally, the annular end surfaces 255 of the collars 238 are toothed or have a known starburst connector, and the inwardly directed opposed surfaces of respective interior and exterior pieces 252, 254 likewise have correspondingly shaped serrations. A starburst connector as referred to herein is normally a circular structure in which the connector portion is an annular ring of adjacent, radially extending serrations or teeth.

Thus, upon sufficient tightening of threaded knobs 256, the respective interior and exterior pieces 252, 254 will move together horizontally until their respective engagement surfaces contact and engage opposing surfaces of the respective collars 238. This engagement force holds the radiolucent adaptor subassemblies 250 in a fixed position relative to the radiolucent table extension 28. Upon loosening the threaded knobs 256, the subassemblies 250 may be hingedly moved relative to a first connection axis 240 to a different position, whereupon the threaded knobs 256 can again be tightened to form a rigid connection.

The radiolucent adaptor assembly 210 of the present invention includes a radiolucent mounting structure 277 which releasably holds and supports the patient stabilization device or head support 280, for example, a radiolucent skull clamp. The radiolucent mounting structure 277 includes a radiolucent bracket 278, a radiolucent sliding member 286 and a radiolucent pivoting member 294. The mounting structure 277 permits the skull clamp 280 to be moved through linear and rotary motions with respect to support member 28. The radiolucent bracket 278 includes a pair of spaced collars 282 which are adapted to be connected to the spaced adaptor subassemblies 250 along the second connection axis 270. This likewise enables the skull clamp 280 to be oriented in a desired position relative to the table extension 28, via hinged movement about first connection axis 240, hinged movement about second connection axis 270, or both. The radiolucent bracket 278 receives a radiolucent sliding member 286. The radiolucent sliding member 286 is lockable to the radiolucent bracket 278 via a clamp comprised of a threaded screw 288.

The pivoting member 294 has a known annular toothed or starburst connector, and a mating starburst connector extends from a frame member 326 of the skull clamp 280. The radiolucent skull clamp 280 is attached to the pivoting member 294 of the sliding member 286 by means of a clamp comprised of a threaded screw 360. The radiolucent surgical skull clamp 280 includes a C-shaped frame 322 comprised of frame members 324, 326 which are movable to "telescope" toward and away from one another. The frame members 324, 326 are normally made of a radiolucent polyethersulfone (PES) and carbon composite material with the carbon component being about 30 percent of the composite by weight. Such a composite material is available from ICI Advanced Materials of Exton, Pa. under the commercial name "THERMOCOMP" JC-1006, and is also available from LNP Engineering Plastics of Thorndale, Pa. under the commercial name "STAT-KON" JC-1006. Alternatively, other radiolucent materials may be used.

Frame members 324, 326 have parallel first arms 328, 330, respectively, which are juxtaposed to each other in a sliding relationship with the first arm 330 of the frame member 326 cradling or surrounding the first arm 328 of the frame member 324. Extending from one end of the arm 328, the frame member 324 has an intermediate arm 332 extending diagonally away from the frame member 326 and an upper arm 334 extending angularly back toward the frame member 326. The upper arm 334 has, at its outer or distal end, a pin holder, for example, a threaded bore that receives a skull pin 335. Similarly, extending from the first arm 330, the frame member 326 has an intermediate arm 336 extending away from the frame member 324 and an upper arm 338 extending back toward the frame member 324. The upper arm 338 has an angular positioning mechanism 337 mounted at its outer or distal end. The angular positioning mechanism releasably locks a pin holding clevis 339 that supports skull pins 341. The clevis 339 and skull pins 341 are positioned by operating knobs 343, 345 in a known manner.

In use, referring to FIG. 2, the bracket 278 and sliding member 286 are first assembled onto the collars 238. Next, the skull clamp 280 is mounted onto the sliding member 286 using the knob 360 to tighten the skull clamp to a locked position. The precise location of the skull clamp 280 is adjusted in a plane generally perpendicular to the frame members 324, 326 using the adjustments described above. The height and angle of the skull clamp 280 is further precisely adjusted using the knobs 256. Further, after the patient is initially placed on the operating table 22 and table extension 28, it is necessary to locate the patient's head in the skull clamp 280. Next the skull clamp 280 and patient's head must be located at a desired position and orientation. Those processes are greatly aided by the capability of adjusting the length of the table extension 28. After loosening the locking screw 42, the position of the patient's head with respect to the skull clamp 280 and/or the adaptor assembly 210 is easily changed by translating the outer support member 32 toward or away from the inner support member 30. After the patient's head and the skull clamp 280 have been properly positioned and oriented, the locking screw 42 is tightened to secure the outer support member 32 to the inner support member 30. Thus, the variable length table extension gives the surgeon significantly more flexibility in being able to position and orient the patient's head and/or skull clamp 280 without having to move and reposition the patient's whole body on the operating table 22 and table extension 28.

Figure 5:
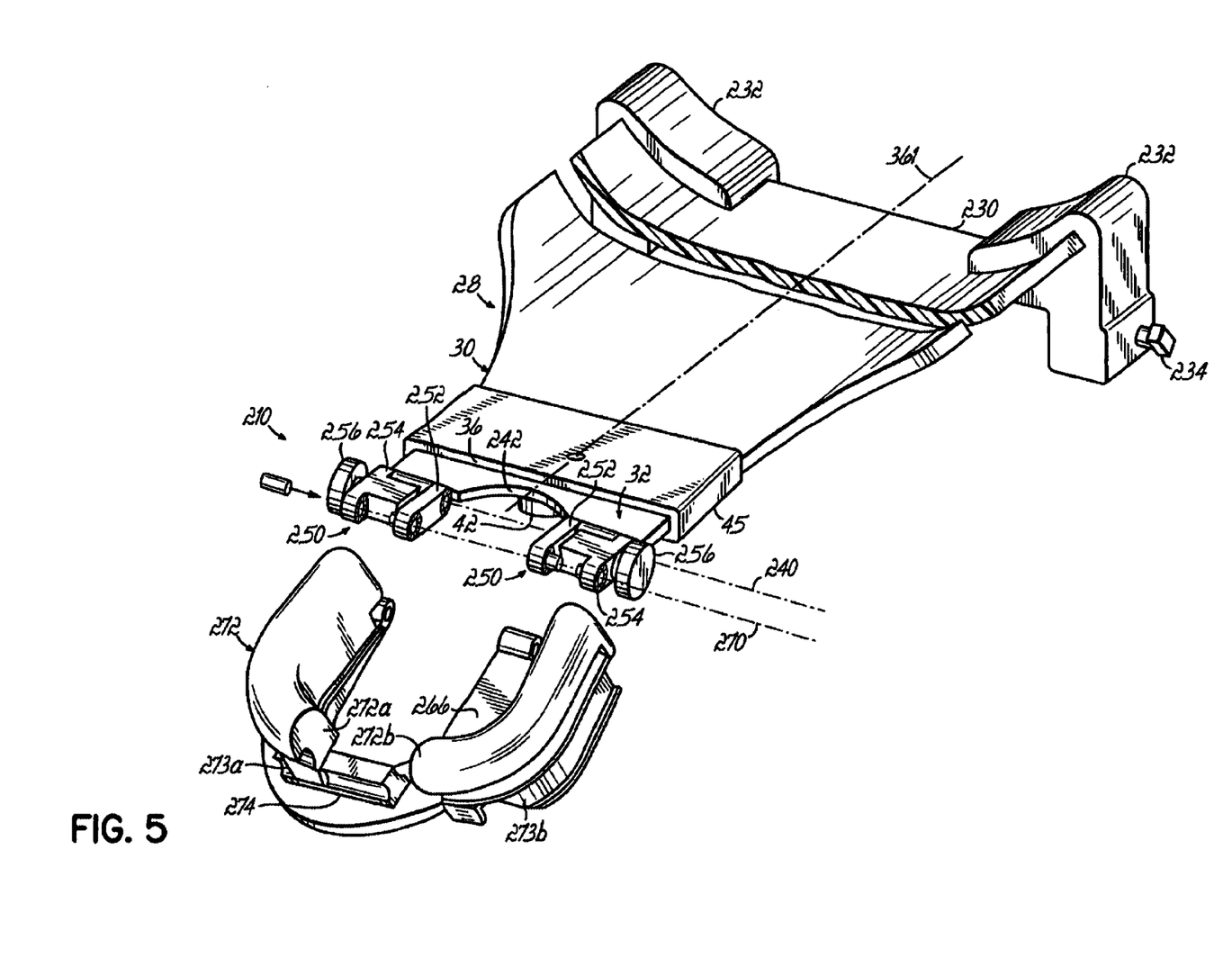
FIG. 5 is a perspective view of another embodiment having a radiolucent horseshoe headrest mounted on the variable length radiolucent table extension of FIG. 1.

Referring to FIG. 5, in an alternative embodiment, the hinged adaptor assembly 210 of the present invention interconnects a horseshoe headrest 272 to the variable length radiolucent table extension 28. The hinged adaptor assembly 210 permits the horseshoe headrest 272 to be tilted relative to the table extension 28 about either or both of the first and second connection axes 240, 270. Preferably, the horseshoe headrest 272 includes an upstanding mount 274 oriented perpendicular the length or longitudinal axis 361 of the table extension 28. This mount 274 may include a dovetail shape, or any other desired cross-sectional shape for that matter, which corresponds to a complementary shape formed in a headrest portion 272a or 272b, so that the headrest portions 272a and 272b can be slidably located on the mount 274.

If desired, each of the horseshoe headrest portions 272a and 272b may include a base 273a and 273b made of radiolucent material for supporting the cushion thereabove along its curved length. The base 273a and 273b may be made of the same material as the panel 266 and the mount 274. With this construction, the headrest itself 272 comprises a pad or cushion secured to the base 273a and 273b.

When the adaptor assembly 210 of the present invention is used in conjunction with the horseshoe headrest 272, the U-shaped panel 266 combines with the arcuate end 242 to form an enclosed oval. An outermost end of the entire assembly is now defined by the outermost end of the U-shaped panel 266. Thus, the headrest 272 resides inboard of the outermost end of panel 266, and in effect, the adaptor assembly 210 provides a pair of intermediately located hinged axes 240 and 270 for locating the horseshoe headrest 272 in a desired position relative to the table extension 228 and the patient supported thereon.

The longitudinal location of the horseshoe headrest with respect to the table 22 can be adjusted to accommodate patients of different heights by loosening the locking screw 42 and moving the outer support member 32 with respect to the inner support member 30.

It is essential that the surgeon be able to position the patient very accurately. Minor changes in patient position have major consequences for optimal access and visualization during surgery. In the past, properly positioning and orienting a patient's head in a skull clamp often required continuous repositioning of the patient's whole body on the operating table and table extension. However, the variable length surgical table extension allows a patient stabilization device to be moved in many degrees of freedom including along a length of the table extension. With the variable length table extension, a surgeon can easily and accurately position and orient the stabilization device with respect to the patient's head substantially independent of the patient's body position. Therefore, the surgeon can make minor adjustments of the patient's head with respect to the stabilization device without having to move the patient's whole body. The variable length surgical table extension provides substantially more flexibility in positioning a patient's head in a skull clamp and is especially advantageous for use in neurosurgery and spinal surgery as well as intraoperative scanning procedures.

While the present invention has been illustrated by a description of various described embodiments and while these embodiments have been described in considerable detail in order to describe the best mode of practicing the invention, it is not the intention of Applicant to restrict or in any way limit the scope of the appended claims to such detail. Additional advantages and modifications within the spirit and scope of the invention will readily appear to those skilled in the art. For example, in the described embodiment, the inner support member 30 has a cavity 34 that receives the inner end 40 of the outer support member 32. As will be appreciated, in an alternative embodiment, the cavity 34 may be located in the outer support member 32, and the outer end of the inner support member 30 sized to slide into the cavity. Further, one embodiment of a locking system is described herein, but as will be appreciated, there are many potential variations of the described system as well as completely different locking systems that may be used to secure the inner and outer support members together.

While one style of skull clamp 280 and headrest 272 are shown and described, in alternative embodiments, other styles of patient stabilization devices may be used with the variable length radiolucent table 28.

Therefore, the invention in its broadest aspects is not limited to the specific detail shown and described. Consequently, departures may be made from the details described herein without departing from the spirit and scope of the claims which follow.

What is claimed is:

1. A surgical table extension for use in combination with a surgical table having opposed longitudinal ends and a scanning machine having an enclosed scanning zone, comprising:
    a radiolucent inner support member comprising an inner end and an outer end, the inner end adapted to be removably attached to a longitudinal end of the surgical table and to extend outward from the longitudinal end in cantilever fashion;
    a radiolucent outer support member comprising an inner end and an outer end, the inner end of the outer support member being adjustably mounted to the outer end of the inner support member, the outer support member being adjustable with respect to the inner support member to change a length of the table extension, the surgical table and the table extension being movable relative to the scanning machine to locate the table extension within the scanning zone;
    a cavity comprising flat, opposing walls extending across a substantial portion of a width of one of the outer end of the inner support member and the inner end of the outer support member;
    another of the outer end of the inner support member and the inner end of the outer support member extending into the cavity; and
    a locking mechanism operably connected to the inner support member and the outer support member.

2. The surgical table extension assembly of claim 1 wherein the locking mechanism extends through one of the walls of the cavity and engages an opposite wall for securing the outer support member at a desired position with respect to the inner support member.

3. The surgical table extension assembly of claim 1 wherein the one of the inner support member and the outer support member has a thickness around the cavity exceeding a thickness of another of the inner support member and the outer support member.

4. The surgical table extension assembly of claim 1 wherein the cavity is disposed in the outer end of the inner support member and the inner end of the outer support member is disposed in the cavity.

5. The surgical table extension assembly of claim 4 wherein the outer support member comprises a slot and the locking mechanism comprises:
    a threaded insert nonrotatably mounted in one of the walls of the cavity; and
    a locking screw extending through an opposite wall of the cavity, the slot in the outer support member and into the threaded insert to lock and unlock the outer support member with respect to the inner support member.

6. The surgical table extension assembly of claim 5 wherein the locking screw is made from a radiolucent material.

7. The surgical table extension of claim 1 further comprising a patient stabilization device supported by the outer support member.

8. The surgical table extension of claim 7 wherein the patient stabilization device is a radiolucent skull clamp.

9. The surgical table extension of claim 7 wherein the patient stabilization device comprises a radiolucent horseshoe headrest.

10. The surgical table extension of claim 9 further comprising an opening formed between the horseshoe headrest and the outer support member.

11. A radiolucent surgical table extension for use in combination with a surgical table and a scanning machine having a scanning zone, the table extension comprising:
    a radiolucent inner support member comprising an inner end and an outer end, the inner end being adapted to be removably attached to one end of the surgical table in cantilever fashion, the outer end of the inner support member comprising a cavity disposed therein, the cavity comprising flat, opposing walls extending across a substantial portion of a width of the outer end of the inner support member;
    a radiolucent outer support member comprising an inner end, an outer end and a longitudinally extending slot, the inner end of the outer support member being disposed in the cavity, the outer support member being adjustable with respect to the inner support member to change a length of the radiolucent surgical table extension, the radiolucent inner support member and the radiolucent outer support member having a rigidity sufficient to support an upper torso and head of a patient, the surgical table and the radiolucent support member adapted to be movable relative to the scanning machine to locate the radiolucent outer support member and the patient within the scanning zone; and
    a locking mechanism operably connected to the inner support member and the outer support member and comprising
        a threaded insert nonrotatably mounted in one of the walls of the cavity, and
        a locking screw extending through an opposite wall of the cavity, the slot in the outer support member and the threaded insert to lock and unlock the outer support member with respect to the inner support member.

12. The surgical table extension of claim 11 further comprising:
    a radiolucent mounting structure connected to the radiolucent outer support member; and
    a radiolucent skull clamp attached to the radiolucent mounting structure and adapted to support a head of a patient.

13. A patient support for use with a scanning machine comprising:
    a table having opposed longitudinal ends and an upper surface adapted to support a patient;

a table extension comprising
  a radiolucent inner support member comprising an inner end and an outer end, the inner end removably attached to a longitudinal end of the surgical table and extending outward from the longitudinal end in cantilever fashion;
  a radiolucent outer support member comprising an inner end and an outer end, the inner end of the outer support member being adjustably mounted to the outer end of the inner support member, the outer support member being adjustable with respect to the inner support member to change a length of the table extension, the outer support member having a rigidity sufficient to support an upper torso and head of the patient;
  a cavity comprising flat, opposing walls extending across a substantial portion of a width of one of the outer end of the inner support member and the inner end of the outer support member;
  another of the outer end of the inner support member and the inner end of the outer support member extending into the cavity;
  a locking mechanism operably connected to the inner support member and the outer support member; and
  a radiolucent patient stabilization device removably connectable to the outer support member and adapted to support and hold the head of the patient in a desired position.

14. The support assembly of claim 13 further comprising a radiolucent adaptor assembly mounted on the outer support member for supporting the patient stabilization device.

15. The support assembly of claim 14 wherein the patient stabilization device comprises a radiolucent skull clamp.

16. The support assembly of claim 14 wherein the patient stabilization device comprises a radiolucent horseshoe headrest.

17. The support assembly of claim 16 further comprising an opening formed between the horseshoe headrest and the outer support member.

18. In combination, an apparatus comprising:
  a portable scanning machine having a scanning zone and adapted to take scans in the scanning zone;
  an imaging system operatively connected to the scanning machine and adapted to store images representative of scans of the scanning zone taken by the scanning machine;
  a patient table having an upper support surface and opposed longitudinal ends; and
  a radiolucent table extension assembly comprising
    a radiolucent inner support member comprising an inner end and an outer end, the inner end removably attached to a longitudinal end of the surgical table and extending outward from the longitudinal end in cantilever fashion,
    a radiolucent outer support member comprising an inner end and an outer end, the inner end of the outer support member being adjustably mounted to the outer end of the inner support member, the outer support member being adjustable with respect to the inner support member to change a length of the radiolucent table extension with respect to the longitudinal end of the table, the patient table and the radiolucent table extension assembly being movable relative to the scanning machine to locate the radiolucent table extension assembly within the scanning zone,
    a cavity comprising flat, opposing walls extending across a substantial portion of a width of one of the outer end of the inner support member and the inner end of the outer support member,
    another of the outer end of the inner support member and the inner end of the outer support member extending into the cavity,
    a locking mechanism operably connected to the inner support member and the outer support member, and
    a radiolucent patient stabilization device supported on the outer support member, the radiolucent table extension adapted to support a head and upper torso of a patient on the upper support surface, the radiolucent table extension being sized to be received within the scanning zone, the patient table and the radiolucent table extension being movable relative to the scanning machine to locate the radiolucent table extension within the scanning zone.

19. The apparatus of claim 18 further comprising a radiolucent adaptor assembly located at an edge of the outer support member and supporting the patient stabilization device.

20. The apparatus of claim 19 wherein the patient stabilization device is a skull clamp.

21. The apparatus of claim 19 wherein the patient stabilization device is a radiolucent headrest.

22. A radiolucent surgical table extension for use in combination with a surgical table and a scanning machine having a scanning zone, comprising:
  a radiolucent inner support member comprising an inner end and an outer end, the inner end adapted to be removably attached to one end of the surgical table in cantilever fashion; and
  a radiolucent outer support member comprising an inner end and an outer end, the inner end of the outer support member being adjustably mounted to the outer end of the inner support member, the outer support member being adjustable with respect to the inner support member to change a length of the radiolucent surgical table extension, the radiolucent inner support member and the radiolucent outer support member having a rigidity sufficient to support an upper torso and head of a patient, the surgical table and the radiolucent support member adapted to be movable relative to the scanning machine to locate the radiolucent outer support member and the patient within the scanning zone; and
  a horseshoe headrest rotatably mounted to the outer end of the outer support member.

23. The radiolucent surgical table extension of claim 22 wherein the horseshoe headrest comprises:
  a panel pivotally mounted to the outer end of the outer support member;
  a generally horseshoe shaped pad mounted on the panel.

24. The radiolucent surgical table extension of claim 23 wherein the horseshoe headrest further comprises:
  a mount attached to and extending upward from the panel and comprising a linear guide extending substantially perpendicular to a longitudinal centerline of the outer support member; and
  a pair of horseshoe headrest portions disposed in, and movable along, the linear guide on the mount.

25. The radiolucent surgical table extension of claim 23 wherein the inner end of the outer support member has an arcuate shaped opening and the panel is generally U-shaped, the arcuate shaped opening and the panel forming an enclosed oval upon the outer support member being connected to the inner support member.

* * * * *